United States Patent [19]

Morgan et al.

[11] Patent Number: 5,707,658

[45] Date of Patent: Jan. 13, 1998

[54] METHOD FOR TREATING HORSE MANURE WITH DRY ACID

[75] Inventors: David R. Morgan, Sylvania, Ohio; Suad A. Terzich, Salisbury, Md.

[73] Assignee: Jones-Hamilton Co., Newark, Calif.

[21] Appl. No.: 757,748

[22] Filed: Nov. 26, 1996

[51] Int. Cl.⁶ .......................... A01K 13/00; A01N 59/02
[52] U.S. Cl. .................... 424/600; 424/76.6; 424/709
[58] Field of Search ................. 424/76.6, 600, 424/709

[56] References Cited

U.S. PATENT DOCUMENTS

| | | | |
|---|---|---|---|
| 3,857,946 | 12/1974 | Shibata | 424/266 |
| 3,892,846 | 7/1975 | Wortham | 424/76 |
| 4,607,594 | 8/1986 | Thacker | 119/1 |
| 5,448,967 | 9/1995 | Ryan | 191/171 |

FOREIGN PATENT DOCUMENTS

| | | |
|---|---|---|
| 0 076 447 | 4/1983 | European Pat. Off. . |

OTHER PUBLICATIONS

Jones–Hamilton Co., "Technical Update", Issue 1, Sep. 1995.

Jones–Hamilton Co., "PLT Poultry Health Sentinel", Premier Issue, Sep. 1995.

J. of Pharmacol. & Exp. Therapeutics, vol. 82, pp. 377–390 (1944).

Ivos et al., Poultry Science, vol. 45, pp. 676–683 (1966).

Carlile, Worlds Poultry Science Journal, vol. 40, pp. 99–113 (1984).

Burnett et al., Animal Waste Management, pp. 271–291 (1969).

*Primary Examiner*—S. Mark Clardy
*Attorney, Agent, or Firm*—MacMillan, Sobanski & Todd

[57] ABSTRACT

A method for treating equine manure involves contacting the manure with sodium bisulfate, preferably at a level of at least 50 grams per square meter of surface. The sodium bisulfate is preferably applied at least once per week. Another embodiment is a method for treating the manure with a material to reduce the pH of the manure, preferably to a pH less than 5. A related embodiment is a method for treating the manure with an acid to reduce the number of flies in the area around the manure, preferably to less than 25% of the number of flies in the same area without the treatment. Another embodiment is a method for treating the manure with a material to reduce the ammonia level in the air above the manure to less than about 2 parts per million.

20 Claims, No Drawings

METHOD FOR TREATING HORSE MANURE WITH DRY ACID

BACKGROUND OF THE INVENTION

This invention relates to a method for treating horse manure to control certain problems associated with the manure and in particular to a method for lowering the pH of horse manure to control flies and ammonia emissions.

Domesticated horses are often housed in stalls in a barn or stable. The stall floor is covered with a layer of bedding to allow the horse to lie down, to provide warmth, and to protect the horse from injury. Wheat straw is the most widely used form of bedding. Other conventional bedding materials include wood shavings, sawdust, peat, and shredded paper.

Horses produce waste materials, namely manure and urine, which are deposited on the bedding. The horse manure causes problems in the stall and the surrounding area. One problem is the large scale breeding of flies in the manure. Flies are a nuisance to horses and to people in the area. The flies can spread diseases and parasites, and can damage or irritate the eyes of the horses.

Another problem is the release of ammonia into the air from decomposition of the manure. Ammonia is a known respiratory irritant in humans, and it is believed to be a respiratory irritant in horses. Veterinarians are most concerned about ammonia's effects on newborn horses. Regulatory agencies are also concerned about ammonia as a potential air pollutant.

To address these problems, the stall can be cleaned out periodically to remove horse manure and soiled bedding. However, it is difficult to remove all the manure. It is also inconvenient to remove the manure as often as needed. Insecticides can be used to control flies, but insecticides present toxicity problems and environmental concerns. It is known to spread lime on the floor of a stall to control odors. Lime is not totally effective against odors and it does not address the other problems caused by manure. Thus, it would be desirable to provide an effective and convenient method for controlling the problems caused by horse manure.

SUMMARY OF THE INVENTION

This invention relates to a method for treating horse manure to control the problems associated with manure. In a preferred embodiment, the method involves contacting the manure with a dry acid such as sodium bisulfate to reduce the pH of the manure, preferably to a pH of less than about 5. Reducing the pH of the manure significantly reduces the number of flies in the area compared to untreated manure. The ammonia level in the air above the manure is also significantly reduced. The dry acid used to contact the manure is not more than mildly irritating to the skin of horses, as measured by a Primary Irritation Index of less than about 2. Preferably, the manure is contacted by applying sodium bisulfate on the floor of a stall at a level of at least about 50 grams per square meter of floor. The sodium bisulfate is preferably applied at least about once per week, and more preferably at least about once per day.

Various objects and advantages of this invention will become apparent to those skilled in the art from the following detailed description of the preferred embodiment.

DETAILED DESCRIPTION OF THE PREFERRED EMBODIMENT

It has now been discovered that the problems associated with horse manure can be effectively controlled by contacting the manure with a material to reduce the pH of the manure. Untreated horse manure typically has a pH of about 8.5. The horse manure is contacted with a material to reduce the pH of the manure by at least about 2 pH units, and preferably at least about 3 pH units. For example, the pH of the manure can be reduced to less than about 6, preferably less than about 5, more preferably less than about 4, and more preferably less than about 3. Most preferably, the pH of the manure is reduced to a pH within the range from about 1.5 to about 2.5.

The pH of the manure is measured by taking a sample from the surface of the manure, mixing the sample with an equal volume of distilled water to make a slurry, and measuring the pH of the slurry by use of a pH meter. For example, when the manure is located on a stall floor having straw bedding, a 60 ml volume of soiled straw can be collected from the most soiled area of the stall and mixed with an equal volume of distilled water. The manure attached to the straw is from the surface of the manure. As another example, when the manure is located in a manure pile, a 60 ml volume of manure can be removed from the surface of the manure pile and mixed with an equal volume of distilled water.

The material used to contact the manure is preferably an acid, although other pH-lowering materials can also be employed. Suitable acids include sodium bisulfate, sulfamic acid, propionic acid, phosphoric acid, hydrochloric acid, sulfuric acid, and many other acids well known to chemists. A dry acid is generally more convenient to use than a liquid acid. Sodium bisulfate and sulfamic acid are preferred dry acids.

Importantly, it has been found that certain dry acids can be applied on the floor of a stall without harming the skin and hooves of the horses. Horses are very valuable possessions, and many horses are considered to be pets. Thus, it is critical to provide a treatment method which does not cause harm to the horses. During the day, the hooves of the horses contact the floor. At night, the horses may lie on the floor to sleep where their skin contacts the floor. Consequently, when an acid is applied on the floor, the horses may be in almost constant contact with the acid over prolonged time periods. It was not predictable beforehand that a dry acid could be effective in controlling the problems associated with horse manure, without causing harm to the horses.

The dry acids suitable for use in this invention are not more than mildly irritating to the skin of horses, and preferably are non-irritating to their skin. The effect of a potential chemical irritant on the skin of horses can be measured by a Primary Irritation Index. Chemicals having a Primary Irritation Index of less than 2 are considered not more than mildly irritating. Accordingly, suitable dry acids have a Primary Irritation Index of less than about 2, preferably less than about 1, and more preferably about 0. The method for measuring Primary Irritation Index is described below.

A highly preferred dry acid is sodium bisulfate. One type of preferred sodium bisulfate is manufactured by Jones-Hamilton Co., Walbridge, Ohio. The Jones-Hamilton sodium bisulfate is certified under ISO 9002. It is also manufactured under a Food Chemicals Codex Specification, and classified as nonhazardous by the Department of Transportation.

The manure can be contacted with the dry acid or other pH-lowering material by any convenient method. In a typical method, the manure is contacted by applying the dry acid on the floor of a stall. When the manure is deposited on the floor, it comes into contact with the dry acid. By "floor", as used herein, is meant either the floor of the stall itself, or the bedding covering the floor. For example, the dry acid can be spread relatively evenly on the floor of a stall, and then covered with the normal amount of straw bedding. Alternatively, the dry acid can be spread relatively evenly on the top of the bedding. A scoop or other apparatus can be used to spread the dry acid.

Manure is also frequently located on the ground outside the building containing the stalls. In such instances, the manure can be contacted by applying the dry acid on the ground. The dry acid can also be applied directly to the manure, for example when the manure is located in a large manure pile.

The amount and frequency of application of the dry acid will depend on several factors, including the type of dry acid, the number of horses, and the location of the manure. The manure is usually located on a surface such as the floor of a stall, or the ground outside the stalls. When the manure is located on a surface, the manure can be contacted by applying sodium bisulfate at a level of at least about 50 grams per square meter of surface. Preferably, the sodium bisulfate is applied at a level of at least about 150, more preferably at least about 200, more preferably at least about 250, and most preferably at least about 300 grams per square meter of surface. For example, when the floor of the stall has an area of about 9 square meters, preferably at least about 0.45 kilograms of sodium bisulfate are applied on the floor, and more preferably at least about 1.8 kilograms.

However, it is unnecessary to apply more than a certain level of sodium bisulfate to effectively control the problems associated with manure. The sodium bisulfate can be applied at a level of not more than about 800 grams per square meter of surface, and preferably not more than about 700 grams per square meter of surface. Higher application levels do not significantly increase the effectiveness of the treatment.

The manure is preferably contacted with dry acid at least about once per week. More preferably, the manure is contacted at least about once per 2–3 days, and most preferably at least about once per day. In general, when the dry acid is applied more frequently, a smaller amount of dry acid can be used per application to control the problems associated with manure. The dry acid can be applied regularly over long periods of time without harming the horses.

It has been found that reducing the pH of the manure by contact with an acid significantly reduces the number of flies in the area compared to untreated manure. As discussed above, untreated manure is a favorable environment for the large scale breeding of flies. While not intending to be limited by theory, it is believed that the reduction in pH of the manure inhibits production or growth of fly larvae. As a result, the flies cannot successfully reproduce in the manure.

In particular, the number of flies is reduced in an area within about 3 meters of the manure. Preferably, the number of flies in the area is reduced to less than about 25% of the number of flies in the same area with untreated manure, and more preferably less than about 20%.

The reduction in number of flies in the area can be measured by hanging a flypaper in the area and counting the number of flies adhered to the flypaper after a period of time. A suitable flypaper for measuring the reduction in flies is TAT Flypaper manufactured by Walco-Linck Co., Clifton, N.J. This flypaper includes an adhesive portion having a length of 76.2 centimeters and a width of 3.5 centimeters, and has adhesive on both sides of the flypaper.

When the manure is located in a horse stall, the reduction in number of flies can be measured by hanging the flypaper from the ceiling at the center of the stall. Preferably, not more than about 0.5 flies per cubic meter of stall are adhered to the flypaper over a 7 hour period. More preferably, not more than about 0.3 flies per cubic meter of stall are adhered to the flypaper, and most preferably not more than about 0.15 flies per cubic meter of stall. For example, when the stall has length, width and height dimensions of about 3×3×3 meters for an area of about 27 cubic meters, preferably not more than about 14 flies are adhered to the flypaper over a 7 hour period, and more preferably not more than about 9 flies.

Another method for measuring the reduction in flies is to measure the total fly evasive behavior of a horse in the area over a period of time. "Total fly evasive behavior" is defined as the sum of tail swish, head toss, and kick/strike. A "tail swish" is defined as a moving of the tail past its vertical position. A "head toss" is defined as a lifting up or lowering of the nose past the normal plane. A "kick/strike" is defined as a raising of the hind foot (kick) or front foot (strike). For example, a horse in the stall described above can be videotaped for 9 hours to monitor its total fly evasive behavior. Preferably, the horse exhibits not more than about 15 total fly evasive behaviors per 9 hours in the stall. More preferably, the horse exhibits not more than about 10 total fly evasive behaviors, and most preferably not more than about 6 total fly evasive behaviors.

In addition to reducing the number of flies in the stall, reducing the pH of the manure also reduces the number of microorganisms in the manure. Untreated horse manure provides a favorable environment for the growth of microorganisms such as bacteria and fungi. These microorganisms can cause undesirable odors and other problems. The reduction in pH is believed to inhibit the growth of the microorganisms.

This invention also relates to a method for treating horse manure by contacting it with a material to reduce the ammonia level in the air above the manure. The material can be an acid such as those described above, another pH-lowering material, or another material capable of reducing the ammonia level. It has been found that treating the manure with an acid significantly reduces the ammonia level in the air above the manure. The volatilization of ammonia from the manure is caused by bacterial decomposition of nitrogenous compounds in the manure. It is believed that reducing the pH of the manure inhibits the growth of the bacteria that decompose the nitrogenous compounds. The pH reduction also may reduce the activity of enzymes needed for catalyzing the decomposition.

Preferably, the ammonia level in the air above the manure is reduced to less than about 2 parts per million, more preferably less than about 1 part per million, and most preferably less than about 0.5 part per million. The ammonia level is measured at a point 15.6 centimeters above the manure with a digital suction pump and Auer ammonia detection tubes (manufactured by Auergesellschaft GmbH, Germany). When the manure is located in a horse stall, the ammonia level is measured in the region of the stall with the highest concentration of manure.

While the present invention has been described as a method for treating horse manure, the method is equally applicable to any type of equine manure. The equine manure is produced by animals belonging to the family Equidae, which includes horses, asses and zebras.

In the past, sodium bisulfate has been applied to poultry litter to reduce the release of ammonia from the litter. The sodium bisulfate binds the ammonia and changes it to ammonium sulfate, a fertilizer. However, sodium bisulfate has never been used or suggested for use in treating horse manure. Further, sodium bisulfate has never been suggested for use in controlling problems such as flies.

When sodium bisulfate is applied to poultry litter, it is applied only one time at the beginning of the flock. As discussed above, the horse manure is preferably contacted with sodium bisulfate at least about once per week, and more preferably at least about once per day. Another difference is that the level of sodium bisulfate applied to horse manure in only about one-half the level typically applied to poultry litter.

Moreover, the problems associated with the maintenance of horses are very different from the problems associated with poultry. In commercial poultry production, the poultry are grown for about 6 weeks and then processed into meat. In contrast, horses are valuable possessions and are kept for many years. There is a desire to make the horses comfortable and not cause harm to the horses.

EXAMPLE 1

Effect of Sodium Bisulfate on Manure pH, Fly Population, and Ammonia Levels in a Horse Barn The objective of this study was to evaluate the effectiveness of sodium bisulfate in reducing manure pH, fly population and ammonia levels in a horse barn environment.

Materials and Methods

Horses—Four male mixed breed ponies of various weights (mean 185.9±18.9 kg) ranging from 3 to 20 years of age (mean 10.5 years 4±8.3 years) were used for the study. Husbandry and experimental use of ponies were conducted in accordance with the NIH Guide for the Care and Use of Laboratory Animals.

Housing—Ponies were housed in individual box stalls measuring 3.05 meters by 3.05 meters, in a bank barn with concrete floors and cinder block walls. On day 1 of each study week, sodium bisulfate was applied to the stall floor and then covered with the normal amount of straw bedding. On days 2 through 7, sodium bisulfate was applied daily to the top of the bedding and a very thin layer of straw then spread on top. Ponies were kept in the stalls 24 hours a day during the 7 day test period and no stall cleaning was done. All barn windows were closed during the study and barn doors only opened for normal people traffic. On the evening of day 7 of each study week, stalls were washed and the ponies housed at pasture overnight. All procedures were the same during the control week except for the application of sodium bisulfate. No fly repellents were applied during the study. Average daily temperature for the 4 week study ranged from 24.8° C. to 27.7° C.

Study design—The 4 week study was scheduled as follows:

Week 1: No sodium bisulfate application
Week 2: Sodium bisulfate application at 4.5 kg/9.3 m²
Week 3: No sodium bisulfate application
Week 4: Sodium bisulfate application at 2.3 kg/9.3 m²

Determination of manure pH and ammonia levels in stalls, and animal observations were done on the afternoon of day 7 of each study week.

Manure pH determination—A 60 ml volume of soiled straw was collected from the most soiled area in the pony's stall and mixed with an equal volume of distilled water. A pH meter was submerged in the manure slurry and the pH recorded. The pH meter was washed and the recording repeated.

Fly evaluation—Fly tapes were hung from the ceiling at the center of each stall on the morning of day 7. After 7 hours, tapes were removed and flies adhering to the sticky surface counted. Each pony was videotaped for one 9 hour session on day 7 to monitor the pony's fly evasive behaviors. Quantitative measures included tail swish, head toss, and kick/strike frequency and total fly evasive behavior. A tail swish was defined as a moving of the tail past its vertical position. A head toss was defined as a lifting up or lowering of the nose past the normal plane. A kick/strike was defined as a raising of the hind foot (kick) or front foot (strike). Ammonia determination—Ammonia levels were measured with a hand held piston digital suction pump and Auer ammonia detection tubes. The tubes used had a range of 2–500 µL/L with a sensitivity limit of 1 µL/L with a direct reading scale on the tube. For recording the ammonia levels, the device was held 15.6 cm above the region in the stall with the dirtiest bedding.

Pony observation—Ponies were observed daily for any cutaneous lesions or signs of lameness.

Statistical analysis—Repeated measures of analysis of variance was used to determine whether manure pH, number of flies, fly evasive behavior, and ammonia levels, were different between the study weeks. Values were considered significant at $p<0.05$. When significance was found, Bonferroni multiple comparisons test was used to compare study weeks.

Results:

Manure pH determination—Manure pH levels were significantly reduced ($p=0.0001$) during both sodium bisulfate treatment periods when compared to the control weeks. The manure pH results are shown below in Table 1.

Fly evaluation—As shown in Table 1, the numbers of flies collected on the fly tape were significantly reduced ($p=0.007$) during both sodium bisulfate treatment periods when compared to the control weeks. Hourly frequency rates for tail swish, head toss, kick/strike, and total fly evasive behavior are shown below in Table 2. Total fly evasive behavior was significantly reduced ($p=0.038$) during both sodium bisulfate treatment periods. While the individual frequencies (tail swish, head toss, kick/strike) were not statistically significant, review of the data shows a strong trend towards a decrease in each activity during the sodium bisulfate treatment periods.

Ammonia determination—As shown in Table 1, ammonia levels were reduced during both sodium bisulfate treatment periods. As $p=0.0547$, significance was obtained at a 94% confidence limit. No ammonia was detectable in any of the 4 stalls following the sodium bisulfate 4.5 kg treatment and in 3 of the 4 stalls following the sodium bisulfate 2.3 kg treatment.

TABLE 1

Manure pH, number of flies, and ammonia levels in a barn environment following treatment of the stall with sodium bisulfate

| Treatment | Manure pH | Numbers of flies on tape | Ammonia levels (ppm) |
| --- | --- | --- | --- |
| Control | 8.6 ± 0.6 (8–9.3)[a] | 46 ± 17.4 (23–65)[b] | 9.1 ± 9.0 (3.5–22.5) |
| Sodium bisulfite (4.5 kg) | 1.7 ± 0.3 (1.4–2)[b)] | 8 ± 7.2 (1–16)[b] | 0 |
| Control | 8.5 ± 0.5 (7.9–8.9)[a] | 37 ± 13.7 (17–46)[a] | 7.5 ± 7.6 (2–18) |
| Sodium bisulfate (2.3 kg) | 1.9 ± 0.2 (1.6–2)[b] | 2.0 ± 3.1 (1–8)[b] | 0.2 ± 0.4 (0–0.75) |
| p[-] | 0.0001 | 0.0007 | 0.0547 |

TABLE 1-continued

Manure pH, number of flies, and ammonia levels in a barn environment following treatment of the stall with sodium bisulfate

| Treatment | Manure pH | Numbers of flies on tape | Ammonia levels (ppm) |
| --- | --- | --- | --- |

Data are expressed as mean ± SD. Ranges are shown in parentheses. Different letters designate significant difference. Same letters designate no significant difference 0.05.

TABLE 2

Results of fly evasive behavior of ponies in a barn environment following treatment of the stall with sodium bisulfate

| Treatment | Tail swishes | Head tosses | Kicks/strikes | Total Fly Evasive Behavior |
| --- | --- | --- | --- | --- |
| Control | 109 ± 154 (11–336) | 13 ± 21.6 (0–45) | 24 ± 40.2 (0–84) | 146 ± 194.7 (0–336) |
| Sodium bisulfate (4.5 kg) | 2.1 ± 2.7 (0–6) | 2.25 ± 3.86 (0–8) | 0 ± 0 | 4.4 ± 6.4 (0–8) |
| Control | 114 ± 127.8 (0–295) | 15.9 ± 22.0 (0–48) | 12.3 ± 11.7 (0–23) | 142.1 ± 137.7 (0–295.5) |
| Sodium bisulfate (2.3 kg) | 1.7 ± 3.4 (0–6.8) | 2.3 ± 1.5 (0–3) | 0.75 ± 1.5 (0–3) | 4.7 ± 2.0 (0–6.8) |
| p⁻ | 0.1417 | 0.2723 | 0.333 | 0.0378 |

Data are expressed as mean ± SD. Ranges are shown in parentheses.

Pony observation—No signs of cutaneous lesions or signs of lameness were seen during the study. Ponies ate hay placed on the floor in the stall corner. The ponies' eating habits usually resulked in spreading the hay around 25% of the stall over the soiled manure. No cutaneous muzzle lesions were present nor were any gastrointestinal signs noted during the study. No abnormalities of either appearance, actions, or attitude of any pony was noted during the course of the 4 week study.

Discussion of Results

Sodium bisulfate applied to the horse stall environment daily at an application rate of either 2.3 kg/9.3 m² or 4.5 kg/9.3 m² reduced manure pH, number of flies in the stall environment, and ammonia levels when compared to a control period with no sodium bisulfate. Fly evasive behavior patterns of ponies occupying the stalls including tail swishes, head tosses, and kicks/strikes were reduced during the period of sodium bisulfate application.

It was the impression of the individuals conducting the study, including the barn manager who had operated the barn for 15 years, that during the treatment weeks the barn was significantly free of typical pungent ammonia odors. All individuals noted that the barn smelled "sweet", more similar to the odors of a dairy barn than a horse barn using deep littering of bedding. After the end of the study, the stalls were not cleaned out for 7 days and remained sweet smelling and basically free of flies. This is surprising in view of the usual results of leaving dirty, wet horse stalls not cleaned in the summer weather.

EXAMPLE 2

Effect of Sodium Bisulfate on Equine Skin

The objective of this study was to evaluate the safety of sodium bisulfate for use in a horse barn environment by determining its cutaneous irritant effect on hooves and normal skin without hair.

Materials and Methods:

Horses—Six female mixed breed ponies of various weights (mean 244.5±40 kg) ranging from 8 to 26 years of age (mean 15±7 years) were used for the study. Husbandry and experimental use of ponies were conducted in accordance with the NIH Guide for the Care and Use of Laboratory Animals.

Housing—The ponies were housed on a 1½ acre grass pasture in southeastern Pa. The ambient temperature during the study period ranged from 21.7° C. to 36.7° C. with a mean of 30.4°–1.2° C.

Single Application Irritation Testing—Skin patch tests were done on two sites on the right dorsal gluteal region of the pony from which hair was clipped with a #40 surgical blade. On one site, sodium bisulfate (0.5 gm) was placed on a 2.6 cm square of wet gauze and the gauze square then placed on the skin, sodium bisulfate side next to the skin. The pH of this moistened gauze patch was 0. The gauze square was covered by a circular adhesive patch to limit exposure to air or moisture. Cyanoacrylate glue was placed on the perimeter of the patch to firmly secure it to the pony. The second site served as a control and was treated in an identical fashion except no sodium bisulfate was placed on the moistened gauze. The pH of this moistened gauze patch was 7. The patches were left in place for 48 hours at which time they were uncovered and evaluated. Evaluation included visual observation for cutaneous irritation that included Draize grading for erythema and edema. Skin biopsies were obtained from the center of the patch test with an 8 mm punch biopsy following placement of a 7 ml circular line block of adjacent skin with lidocaine. The biopsy site was treated with a topical antimicrobial spray and observed daily until healed. Histologic evaluation of the biopsies was done by an individual blinded to the identity of the control and treatment sites.

Repetitive Application Irritation Testing—Skin patch tests were placed on two sites on the left dorsal gluteal region using the method described above. The patches were left in place for 6 hours then removed. The area was wiped with a damp cloth. This procedure was repeated for 10 consecutive days. Daily evaluation included visual observation for cutaneous irritation that included Draize grading for erythema and edema. Following the patch removal on day 10, skin biopsies were obtained with an 8 mm punch biopsy following placement of a 7 ml circular line block of adjacent skin with lidocaine. The biopsy site was treated with a topical antimicrobial spray and observed daily till healed. Histologic evaluation of the biopsies was done by an individual blinded to the identity of the control and treatment sites.

Exposure of hooves—Following hoof cleaning, 50 gm of sodium bisulfate was applied to the sole of both front hooves of each pony, covered with wet gauze, and the entire hoof covered by adhesive tape. The ponies were observed for signs of lameness and the pressure and pulse intensity in the posterior digital artery evaluated by palpation every 12 hours. After 48 hours the tape and gauze packing was removed and the soles and hoof wall were examined visually.

Results

Single Application Irritation Testing—No changes in the skin of either the treated or control sites could be determined by visual inspection. No edema or erythema were seen, nor were changes in the skin surface or clipped hair detected. No microscopically discernible alteration was seen in the skin biopsies from the control site of 5 of the 6 ponies. One pony's control site skin biopsy had capillary congestion and mixed inflammatory cell infiltrate occurring only in the superficial dermis. No microscopically discernible alterations were seen in the skin biopsies from the sodium bisulfate treated site of 5 of the 6 ponies. One pony's sodium bisulfate treated site skin biopsy had mild multifocal hyperkeratosis and scattered eosinophils limited to the superficial dermis. This pony was not the same pony as the pony with the changes seen at the control site. Healing at all biopsies sites progressed without incident.

Repetitive Application Irritation Testing—No changes in the skin of either the treated or control sites could be determined by visual inspection. No edema or erythema were seen, nor were changes in the skin surface or clipped hair detected. No microscopically discernible alterations were seen in the skin biopsies from the control site of the 6 ponies. All skin biopsies from the sodium bisulfate treated sites taken at the end of the 10 days of exposure had histological changes. Biopsies from 4 ponies had mild to moderate changes including epidermal hyperkeratosis, capillary congestion, edema, and a scattered mixed inflammatory cell infiltrate. All these changes were limited to the epidermis and superficial dermis. Biopsies from 2 ponies had severe changes consistent with chemical contact irritation. Histologic findings were confined to the superficial dermis and epidermis and included epidermal hyperplasia and multifocal full-thickness necrosis with serocellular exudate beneath the necrotic epidermis. The superficial dermis in these two contained a mixed inflammatory cell infiltrate and perivascular eosinophils. The adnexae were unaltered in all specimens. Healing at all biopsies sites progressed without incident.

Exposure of hooves—A total of 12 hooves were evaluated. The hoof application on one pony had been removed during the last 6 hours of contact. On this pony, the sodium bisulfate application was reapplied for an additional 15 hours. No visual abnormalities were noted on the hoof sole or wall of any pony which contacted the sodium bisulfate. No signs of lameness or increase in digital pulse pressure was noted in any pony.

Summary and Discussion of Results

Sodium bisulfate was applied to clipped intact pony skin to evaluate its irritant effect after both single and repetitive applications. Contact with moistened sodium bisulfate for 48 hours had no effect on pony skin when compared to control sites. Contact with sodium bisulfate for 6 hours on 10 consecutive days caused mild to moderate histologic changes in the skin including epidermal necrosis, hyperkeratosis, capillary congestion, edema, and a scattered mixed inflammatory cell infiltrate. All changes were limited to the epidermis and superficial dermis. No changes in the skin of either the treated or control sites could be determined by visual inspection. The contact with sodium bisulfate in this study was in excess of that which would be expected under normal husbandry conditions, yet no deleterious effects were seen. The results of this study suggest that sodium bisulfate would be safe for use in horse stalls.

The method for measuring Primary Irritation Index is the well known "Draize grading" method disclosed in the journal article, Draize, J. H., Woodard, G., Calvery, H. O., "Methods for the Study of Irritation and Toxicity of Substances Applied Topically to the Skin and Mucous Membrane", Journal of Pharmacology and Experimental Therapeutics, 1944, Vol. 82, pp. 377–390. The erythema and edema responses for each animal are used to calculate the Primary Irritation Index. The Primary Irritation Index values are calculated by averaging values for erythema from all sites, averaging the values for edema from all sites, and combining the average values. The erythema and edema responses are scored as follows:

A. Erythema Formation:
1=Very slight erythema (barely perceptible)
2=Well defined erythema
3=Moderate to severe erythema
4=Severe erythema (beet redness)
Total possible erythema score: 4

B. Edema Formation:
1=Very slight edema (barely perceptible)
2=Slight edema (edges of area well defined by definite raising)
3=Moderate edema (area raised approximately 1 mm)
4=Severe edema (raised more than 1 mm and extending beyond area of exposure)
Total possible edema score: 4
Total possible score for Primary Irritation Index: 8

Agents producing Primary Irritation Index values of less than 2 are considered only mildly irritating. Using this type of calculation, the Primary Irritation Index value for the irritating effects of sodium bisulfate on clipped intact skin of horses would be 0.

The principle and mode of operation of this invention have been explained in its preferred embodiments. However, it must be understood that this invention may be practiced otherwise than as specifically explained without departing from its spirit or scope.

What is claimed is:

1. A method for reducing the number of flies in an area containing equine manure comprising contacting the manure with a dry acid to reduce the pH of the manure at least about 3 pH units to a pH less than about 5.

2. The method defined in claim 1 wherein the pH of the manure is reduced to less than about 4.

3. The method defined in claim 2 wherein the pH of the manure is reduced to less than about 3.

4. The method defined in claim 1 wherein the dry acid is selected from the group consisting of sodium bisulfate, sulfamic acid, and mixtures thereof.

5. The method defined in claim 4 wherein the dry acid is sodium bisulfate.

6. The method defined in claim 1 wherein the dry acid has a Primary Irritation Index of less than about 2.

7. The method defined in claim 1 wherein the number of flies in the area is reduced to less than about 25% of the number of flies in the same area without application of the dry acid.

8. A method for reducing the number of flies in an area containing equine manure on a surface, comprising applying a dry acid on the surface at least about once per week, to reduce the number of flies in the area to less than about 25% of the number of flies in the same area without application of the dry acid.

9. The method defined in claim 8 wherein the dry acid is applied on the surface at least about once per every three days.

10. The method defined in claim 9 wherein the dry acid is applied on the surface at least about once per every two days.

11. The method defined in claim 8 wherein the dry acid is applied on the floor of a horse stall, and wherein the horse exhibits not more than about 15 total fly evasive behaviors per 9 hours in the stall.

12. The method defined in claim 8 wherein the dry acid is selected from the group consisting of sodium bisulfate, sulfamic acid, and mixtures thereof.

13. The method defined in claim 12 wherein the dry acid is sodium bisulfate.

14. The method defined in claim 8 wherein the Primary Irritation Index of the dry acid is less than about 2.

15. A method for reducing the number of flies in an area containing equine manure on a surface, comprising applying sodium bisulfate on the surface at least about once per week to reduce the pH of the manure by at least about 3 pH units to a pH less than about 5.

16. The method defined in claim 15 wherein the pH of the manure is reduced to less than about 4.

17. The method defined in claim 16 wherein the pH of the manure is reduced to less than about 3.

18. The method defined in claim 15 wherein the dry acid is applied on the surface at least about once per every three days.

19. The method defined in claim 18 wherein the dry acid is applied on the surface at least about once per every two days.

20. The method defined in claim 15 wherein the number of flies in the area is reduced to less than about 25% of the number of flies in the same area without application of the dry acid.

* * * * *